United States Patent [19]

Seki et al.

[11] Patent Number: 5,248,674
[45] Date of Patent: Sep. 28, 1993

[54] PERCUTANEOUS ADMINISTRATION OF 3'-AZIDE'DEOXYTHYMIDINE

[75] Inventors: Toshinobu Seki; Yasunori Morimoto; Kazuhiko Juni; Kenji Sugihayashi; Takeo Kawaguchi, all of Saitama, Japan

[73] Assignees: Nelson-Sumisho Co., Ltd., Tokyo; Josai University, Saitama, both of Japan

[21] Appl. No.: 523,246

[22] Filed: May 14, 1990

[30] Foreign Application Priority Data

May 12, 1989 [JP] Japan .................................. 117450

[51] Int. Cl.$^5$ ............................................. A01N 43/04
[52] U.S. Cl. ......................................... 514/49; 514/947
[58] Field of Search ................... 424/443, 449; 514/50, 514/49

[56] References Cited

U.S. PATENT DOCUMENTS

| | | | |
|---|---|---|---|
| 3,989,816 | 11/1976 | Rajadhyaksha | 424/60 |
| 3,991,203 | 11/1976 | Rajadhyaksha | 514/946 |
| 4,405,616 | 9/1983 | Rajadhyaksha | 424/244 |
| 4,557,934 | 10/1985 | Cooper | 424/449 |
| 4,690,683 | 9/1987 | Chien et al. | 424/449 |
| 4,724,232 | 2/1988 | Rideout et al. | 514/50 |
| 4,818,538 | 4/1989 | Rideout et al. | 424/436 |
| 4,828,838 | 5/1989 | Rideout et al. | 424/456 |
| 4,833,130 | 5/1989 | Rideout et al. | 514/50 |
| 4,837,208 | 6/1989 | Rideout et al. | 514/50 |
| 4,847,244 | 7/1989 | Rideout et al. | 514/50 |
| 4,883,813 | 11/1989 | Maxim et al. | 514/470 |
| 4,900,548 | 2/1990 | Kitchen | 514/589 |

FOREIGN PATENT DOCUMENTS

| | | |
|---|---|---|
| 0289229 | 2/1988 | European Pat. Off. |
| 289225 | 11/1988 | European Pat. Off. |
| 0301206 | 2/1989 | European Pat. Off. |
| 0366287 | 5/1990 | European Pat. Off. |

OTHER PUBLICATIONS

Seki, et al., "Percutaneous Absorption of Azidothymidine in Rats", International Journal of Pharmaceutics, 57 (1989), pp. 73–75.

Primary Examiner—Thurman K. Page
Assistant Examiner—Leon R. Horne
Attorney, Agent, or Firm—Cushman, Darby & Cushman

[57] ABSTRACT

A method of administering 3'-azide-3'-deoxythymidine (AZT) to an AIDS patient who is in need of treatment with AZT, comprising applying AZT to the skin of said patient together with an absorption promoting agent capable of assisting absorption of AZT through the skin into the blood stream of said patient; and a percutaneous composition comprising AZT as an effective Ingredient together with an absorption promoting agent in an amount effective for assisting percutaneous absorption of AZT.

8 Claims, 3 Drawing Sheets

PERCUTANEOUS ADMINISTRATION OF 3'-AZIDE'DEOXYTHYMIDINE

FIELD OF THE INVENTION

The present invention relates to a method of percutaneous administration of 3'-azide-3'-deoxythymidine (AZT) to AIDS patients. The Invention also relates to a pharmaceutical composition for percutaneous administration of AZT.

PRIOR ART

In recent years the increase in the incidence of acquired immunodeficiency syndrome (AIDS) has become a serious problem all over the world. The agent responsible for AIDS is a certain type of retro virus which selectively attacks T-cells having OXT4 surface antigen, 3'-Azide-3'-deoxythymidine (AZT) is an effective inhibitor of reverse transcriptases which are indispensable for the growth of the virus and for this reason AZT is considered to be a promising drug for curing AIDS patients. However, there has, so far, been no cases of a complete recovery from AIDS due to treatment with AZT. The strong side effects of AZT often prevents continuation of the treatment.

Following, is an explanation of one of the reasons why treatment with AZT has not been satisfactory in clinical applications. Because of the mechanism of its action, AZT requires a certain period of time to exert its action in vivo, whereas it is impossible to maintain an adequate AZT level in blood by the conventional oral administration (Japanese Patent Laid Open No. 290895/1988) even if AZT is given to a patient as frequently as every 4 hours, i.e. 8 times a day, at a dose of 5 mg/kg in each administration (Klecker et al., Clin. Pharmacol. Ther., 41, 407(1987)). However, if AZT is orally administered at a higher dose in order to maintain a sufficiently high blood level of the drug for prolonged periods of time, the resulting high blood level of AZT shortly after administration causes serious and unacceptable side effects.

U.S. Pat. No. 4,724,232 relates to oral administration of AZT for Treatment of AIDS patients. Column 5 lines 14-19 of this patent states that AZT may be administered percutaneously. However, it does not disclose any specific information as to how AZT 15 given to a patient through the skin.

SUMMARY OF THE INVENTION

An object of the present invention is to provide a method for administering AZT at a consistent rate for a prolonged period of time through the skin of AIDS patients. More specifically, the present invention provides a method for treating AIDS patients with a higher degree of efficacy and fewer side effects an compared to the conventional oral administration of AZT to patients.

Another object of the present invention is to provide a pharmaceutical composition which comprises AZT and an absorption promoting agent for administering AZT at a substantially constant rate through the skin of a patient which is effective for treating AIDS.

DETAILED DESCRIPTION OF THE INVENTION

Figure 1:
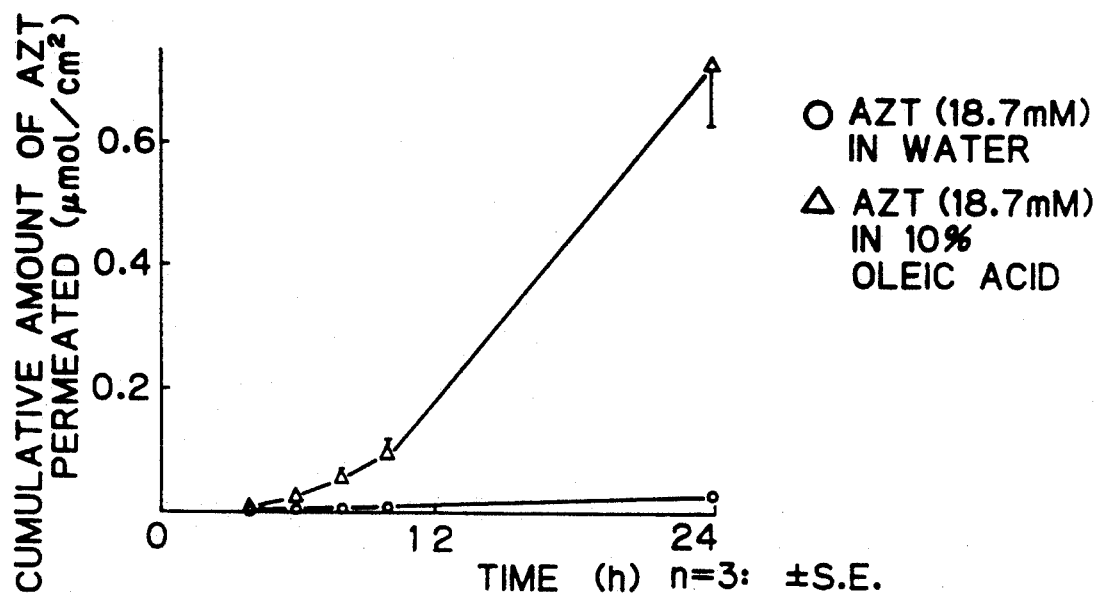
FIG. 1 illustrates in vitro percutaneous absorption of AZT in the presence of 10% oleic acid through removed skin of a rat.

The inventors have conducted an extensive study to provide a method and a composition for administering AZT which enables the maintenance of a consistent and effective blood AZT level for a prolonged period of time. They have discovered that AZT can be absorbed into the blood stream through the human skin at a substantially consistent rate thereby enabling a constant blood level of the drug for a long period of time.

Thus, the present invention provides a percutaneous composition which comprises 3'-azide-3'-deoxythymidine represented by the following formula:

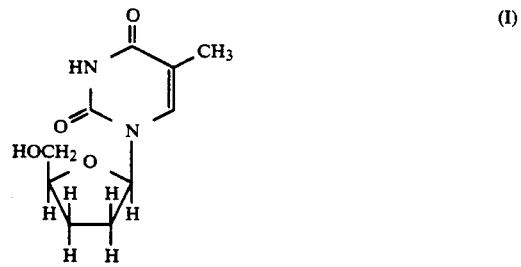

(I)

as an effective ingredient together with a pharmaceutically acceptable absorption promotor, 3'-Azide-3'-deoxythymidine (AZT) is a known compound which is disclosed, for example, in J. R. Horwitz et al, J. Org. Chem., 29, July 1964, pp. 2076-2078; Imazawa et al, J. Org. Chem., 43(15), 1978, pp. 3044-3048. AZT has been used for treating AIDS patients specifically by oral administration.

AZT is contained in the composition of the present invention at a rate of 0.1-20%, preferably 5-10% and most preferably about 3% by weight relative to the total weight of the composition. In any event, the composition should contain AZT so as to facilitate percutaneous administration of 20-2,000 mg and preferably 200-2,000 mg of AZT in a dosage unit.

The absorption promoting agent may be an organic acid acceptable as an ingredient of pharmaceutical compositions. Examples of preferred organic acids include unsaturated fatty acid containing 10-20 carbon atoms such as oleic acid, palmitoleic acid, elaidic acid, linoleic acid, linolenic acid, and ect. The absorption promoting agent may be a pharmaceutically acceptable fatty acid enter. Preferred fatty acid esters are those of a fatty acid of 6-18 carbon atoms and glycerol. More preferably, such esters include glycerol monomyristate, glycerol dimyristate, glycerol monocaprate, glycerol dicaprate, glycerol monolaurate, glycerol dilaurate, glycerol monopentadecanoate, glycerol monopentadecanoate, and etc. These absorption promoting agents may be used preferably at a rate of about 10% by weight of the total composition, though the rate may be chanced in the range between about 1 and 40% by weight.

One preferred absorption promoting agent is Sefsol-318 which is used alone or in combination with one or more other absorption promoting agents such as oleic acid, propylene glycol and/or methyl pyrrolidone. The rate of Sefsol-318 in the total composition is typically about 5% by weight, though the rate may change between 1% and 20%.

A further preferred penetration promoting agent is 1-dodecylazacycloheptane-2-one known as the common name Azone. The typical rate of Azone in the total composition is about 3% by weight, though it may change between 0.1 to 10%. The most preferred absorption promoting agent is a combination of Azone and N-methyl-2-pyrrolidone used at 1:20 to 20:1, and typically at 3:20 by weight.

In any event, the optimum amount of the absorption promoting agent in the composition of the present invention may be determined depending on particular agent considering the expected level of AZT in the blood of a patient who is in need of treatment.

In accordance with the present invention, stable and constant absorption of AZT through the skin of a patient is effected independently of the location or the condition of the skin to which AZT is applied. In particular, even if the the skin condition of the patient has changed because of Kaposi's sarcoma which is a characteristic of AIDS, such a chance will not result in any excessively high concentration of AZT in the blood which would otherwise cause troublesome side effect or shorten the period in which AZT concentration in the blood is maintained in an effective range.

The pharmaceutical composition of the present invention may be formulated in various forms including liquid, cataplasm, cream, ointment, tape and so on. In order to formulate into such a form, conventionally used inert carriers and additives may be incorporated. Typical inert carriers which may be included in the foregoing dosage forms include conventional formulating materials, such as, for example, water, isopropyl alcohol, freons, ethyl alcohol, polyvinyl pyrrolidone, propylene glycol, fragrance, gel-producing materials such as "Carbopol", stearyl alcohol, stearic acid. spermaceti, sorbitan monooleate, "Polysorbates", "Tweens", sorbitan methylcellulose, etc.

The following examples and formulation examples are given for illustration purposes only and should not be interpreted as restricting the scope of the present invention in any aspect.

Example 1 Permeation of AZT through rat skin (in vitro test)

A. The abdominal skin of a rat (Wistar strain, male, 200 g) was removed after shaving and placed between the chambers of a diffusion cell comprising two chambers having an effective permeation area of 0.95 $cm^2$ and a capacity of 2.3 ml for each chamber. The chamber of the corneum side received an AZT solution to be tested and the other chamber received water. The cell was warmed to 37° C. while the permeation of the drug towards the opposite chamber was measured. The AZT solution contained 18.7 mm (5 mg/ml) AZT either in water or an aqueous solution of 10% oleic acid. The results Indicated that oleic acid promoted permeation of AZT through the skin. The results are plotted In FIG. 1. The permeation rate during the stable permeation state (Fss) was determined as follows from the slope of the plots between 10 and 24 hours:

Fss = 0.045 $\mu mol/cm^2/h$.

B. In a manner similar to that described in A, further agents capable of promoting permeation of AZT were searched. The promotion rate by each of the tested agents was expressed in relative terms when the rate of 10% oleic acid is tentatively determined as 1. The results are given in Table 1.

TABLE 1

| Effect of promoting agents | | |
|---|---|---|
| promoting agent | F* | relative promotion rate |
| 10% oleic acid (OA) | 0.045 | 1 |
| 10% OA + 20% propylene glycol (PG) + 10% N-methyl-2-pyrrolidone (MP) | 0.10 | 2.2 |
| 3% Azone | 0.23 | 5.1 |
| 3% Azone + 20% MP | 0.74 | 16.4 |
| 5% Sefsol-318 (S-318) + 20% PG + 10% MP | 0.25 | 5.5 |
| 5% S-318 + 10% OA + 20% PG + 10% MP | 0.63 | 14.0 |

*Maximum permeation rate observed ($\mu mol/cm^2/h$): n = 3

The results indicate that the permeation of AZT through the skin is greatly accelerated by Azone and S-318 than by 10% oleic acid. This acceleration was further enhanced by appropriately combining Azone and S-318 with one or more other promoting agents.

C. In the similar manner as in A and B, the permeation of AZT as a function of its concentration (3.7 mM–112 mM) was studied. 112 mM (about 3%) is a preferred concentration of AZT for practical purposes in producing a percutaneous AZT composition. The combination of a) 3% Azone+20% MP or b) 5% S-318+10% OA+20% PG+10% MP was used as a permeation promoting agent. The results are summarized in Table 2.

TABLE 2

| AZT concentration vs AZT permeation | | | | |
|---|---|---|---|---|
| | 3% Azone + 20% MP | | 5% S-318 + 10% OA + 20% PG + 10% MP | |
| AZT conc. mM (mg/ml) | F* | relative promotion rate | F* | relative promotion rate |
| 3.7 (1) | 0.28 | 6.2 | 0.20 | 4.4 |
| 18.7 (5) | 0.74 | 16.4 | 0.63 | 14.0 |
| 56.2 (15) | 2.22 | 49.3 | 2.41 | 53.6 |
| 112 (30) | 3.22 | 71.6 | 4.85 | 108 |

*$\mu mol/cm^2/h$: n = 3

The results indicate that efficient percutaneous absorption of AZT will be effected by appropriately selecting a promoting agent and the concentration of AZT in the percutaneous preparation.

Example 2 In vivo study - plasma AZT level by percutaneous administrations of AZT Three male rates of Wistar strain weighing about 200 g was allotted to each group. The abdominal portion of the rat was shaven and pretreated with 10% oleic acid for 24 hours. Then a 1 ml aliquot of a solution containing 0.5% (18.7 mM) AZT and 10% oleic acid in water was applied over 4.9 cm² area of the skin by a glass cell secured on the body of the rat. AZT level in the plasma sampled at 0, 5, 1, 2, 4, 6, 8 and 24 hours after the administration was determined by HPLC. A control group orally received 0.5 ml water containing 0.6 mg AZT. The results are summarized in Table 3.

TABLE 3

| hours after AZT administration | AZT level in plasma (μM) | |
|---|---|---|
| | percutaneous | oral |
| 0.5 | 0.2 | 3.1 |
| 1 | 0.6 | 2.5 |
| 2 | 0.7 | 0.5 |
| 4 | 1.5 | 0.2 |
| 6 | 1.5 | n.d.* |
| 8 | 1.5 | n.d. |
| 24 | 4.0 | n.d. |

*n.d. means that AZT level was below the detection level (0.1 μM)

The results show that, in the presence of oleic acid, AZT was gradually absorbed through the skin and could be detected in the plasma over 24 hours whereas the percutaneous absorption of AZT was not observed at all when the drug was applied to the skin as a simple water solution (data is not shown). When AZT was administered orally, the drug level in the plasma decreased to already be undetectable at 6 hours after the administration.

Example 3 In vivo study -percutaneous absorption of AZT

In a manner similar to that described in Example 2, the possibility of percutaneous absorption of AZT without pretreatment with 10% oleic acid was studied.

Figure 2:
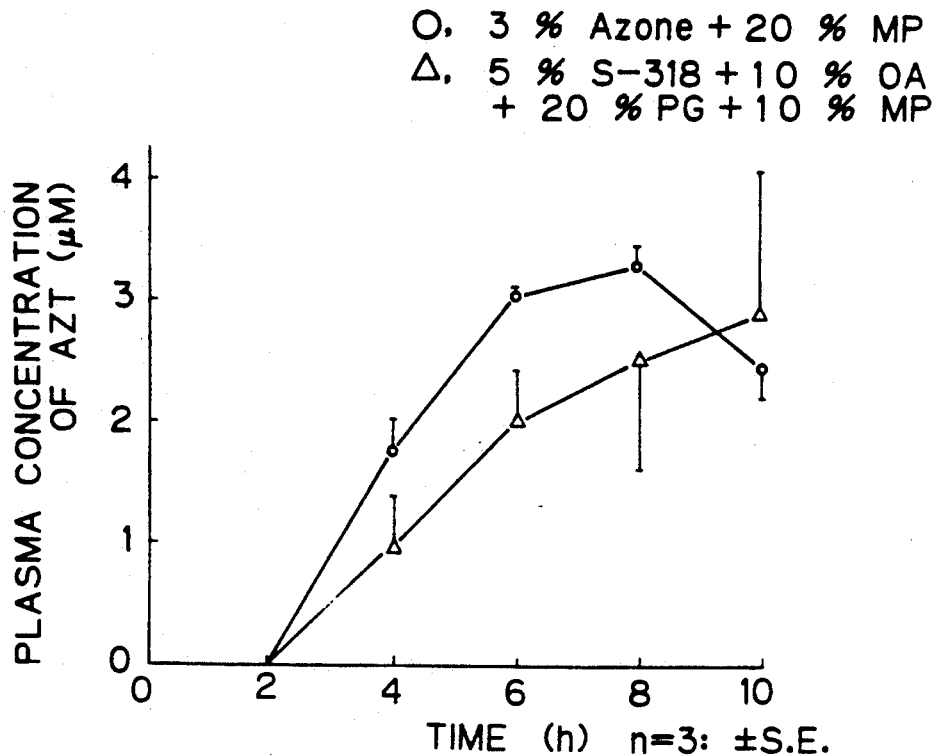
FIG. 2 illustrates in vivo percutaneous absorption of AZT in the presence of a) 3% Azone+20% N-methyl-2-pyrrolidone, or b) 5% 9-318+10% oleic acid+20% propylene glycol+10% N-methyl-2-pyrrolidone.

As absorption promoting agents, a) an aqueous solution containing 3% Azone and 20% MP, and b) an aqueous solution containing 5% S-318, 10% OA, 20% PG and 10% MP were prepared. AZT was dissolved at 3.7 mM concentration in each of said absorption agents and 1 ml of the resulting solution was applied to the skin of rats in a similar manner as in Example 2. AZT level in the plasma was monitored at a 2 hours interval for 10 hours and plotted as shown in FIG. 2. The results show that a high AZT level in the plasma was achieved over a period of 10 hours due to the percutaneous absorption of AZT.

The above two promoting agents assisted the penetration of AZT through the skin even though the skin had not been preteated with 10% oleic acid, Said efficient penetration was achieved by 3.7 mM AZT solution which is lower by 5 times than the AZT solution (18.7 mM) used in Example 2, This efficient penetration was especially remarkable by the promoting agent a) which contains 3% Azons and 20% MP.

Example 4 In vitro study using removed human skin

Figure 3:
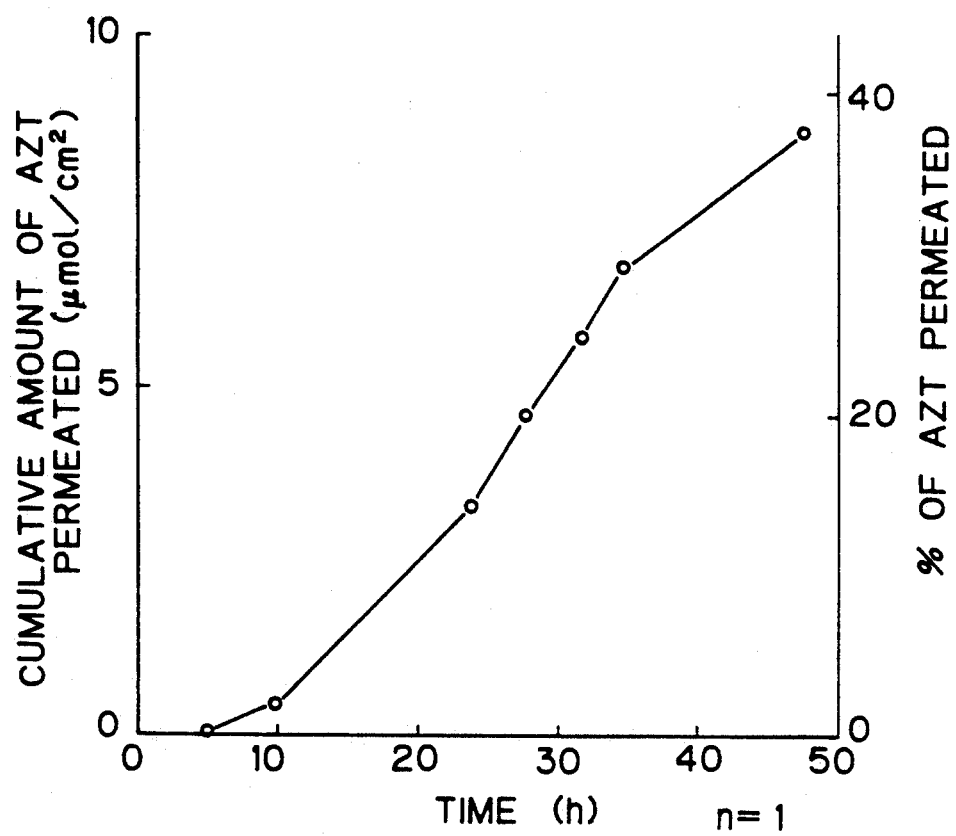
FIG. 3 illustrates in vitro percutaneous absorption of AZT in the presence of 3% Azone+20% N-methyl-2-pyrrolidone through removed human skin.
Figure 4A:
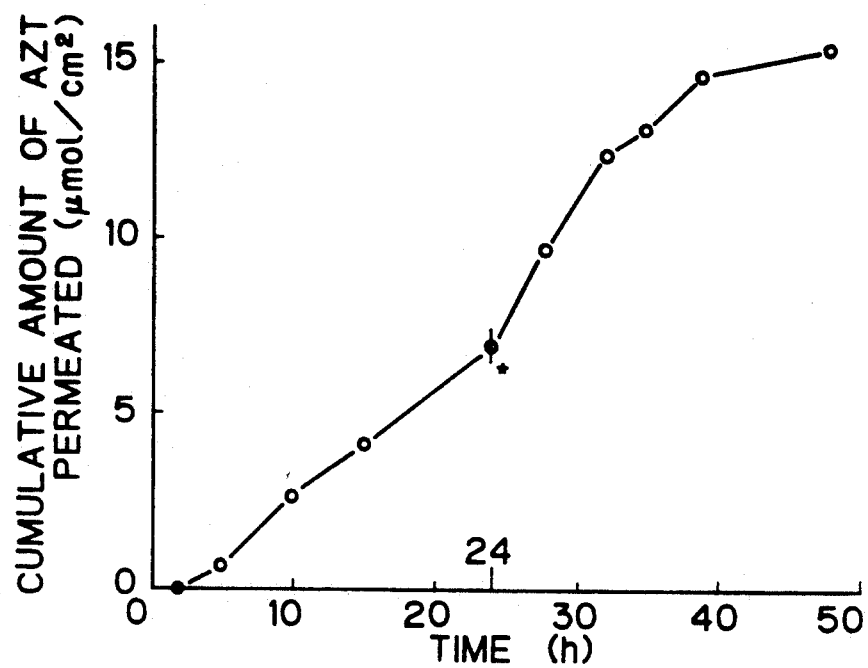
FIG. 4 illustrates in vitro percutaneous absorption of AZT in the presence of 5% S-318+10% oleic acid+20% propylene glycol+10% methyl pyrrolidone through removed human skin.
Figure 4B:
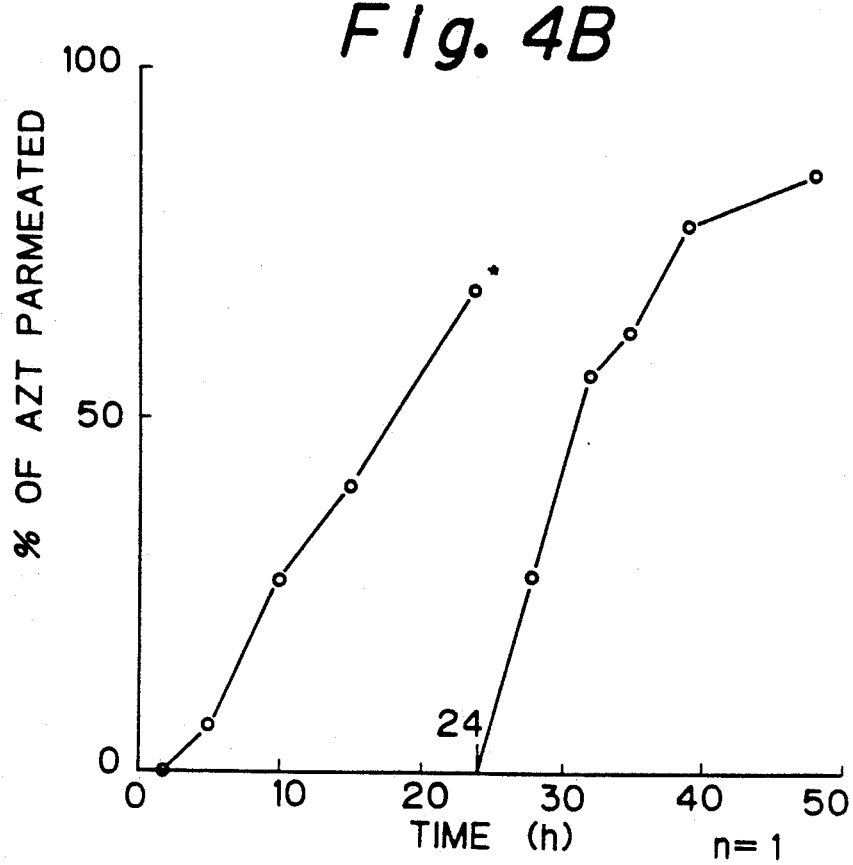

A piece of human skin was set between the chambers of a permeation cell having an effective permeation area of 4.9 cm². The chamber of the corium side received a physiological saline solution and the temperature of the solution was warmed to maintain at 37° C. The percutaneous preparation produced in Formulation Example 7 or 8 hereinafter described was applied on the opposite surface of the skin (corneum). The amount of AZT permeated into the physiological saline was monitored at an appropriate interval. FIG. 3 depicts the results with the composition of Formulation Example 7 and FIG. 4 depicts the results with the composition of Formulation Example 8 wherein the drug an the skin was replenished after 24 hours.

The permeation rate of AZT at the stable permeation state for each drug was 0.30 μmol/cm²/h and 0.70 μmol/cm²/h. respectively for drugs of Formulation Examples 7 and 8. On the basis of the results of this study as well as of the following equation, skin area required for achieving sufficient percutaneous absorption of AZT from these compositions can be calculated.

$$Css = Fss \times A / Cltot$$

wherein
A: skin area (cm²)
Css: Plasma AZT level (μM) required for AIDS treatment
Cltot: clearance (l/h/kg)
Fss: permeation rate at the stable state (μmol/cm²/h)

Cas and Cltot are 1 μM and 78 l/h, respectively according to Klecker et al (Clin. Pharmacol. Ther., 41, 407, 1987). The required skin area calculated from these values was 260 cm² for the composition of Formulation Example 7 and 111 cm² for the composition of Formulation Example 8. Therefore, the efficacy of the percutaneous composition of the present invention has reached a level practically applicable in the treatment of AIDS patients.

The invention will be further illustrated by way of the following non-limiting formulation examples.

| Formulation 1: Ointment | |
|---|---|
| AZT | 10 parts by weight |
| methyl triglycol | 5 |
| liquid paraffin | 10 |
| solid paraffin | 5 |
| Azone | 3 |
| sorbitan sesquioleate | 1 |
| vaseline to make up | 100 |
| Formulation 2: Cream | |
| AZT | 8 parts by weight |
| Crotamiton | 5 |
| vaseline | 15 |
| liquid paraffin | 6 |
| cetyl alcohol | 4 |
| stearyl alcohol | 2 |
| glycerol monomyristate | 3 |
| polyoxyethylene cetyl ether | 3 |
| deionized water to make up | 100 |
| Formulation 3: Liquid | |
| AZT | 0.5 parts by weight |
| oleic acid | 10 |
| deionized water to make up | 100 |
| Formulation 4: Gel | |
| AZT | 7 parts by weight |
| polyvinyl alcohol | 10 |
| myristic acid | 10 |
| deionized water to make up | 100 |
| Formulation 5: Cataplasm | |
| AZT | 1 parts by weight |
| kaolin | 20 |
| sodium polyacrylate | 3 |
| gelatin | 8 |
| glycerol | 30 |
| glyceryl dimyristate | 4 |
| polyacrylic acid | 1 |
| ammonia | small amount |
| deionized water to make up | 100 |
| Formulation 6: Tape | |
| AZT | 10 parts by weight |
| 2-ethylhexyl acrylate | 83 |
| acrylic acid | 5.5 |
| glyceryl monopentadecanoate | 1.5 |

The above ingredients were thoroughly mixed and the mixture was coated on a tape film to give a tape preparation.

Formulation 7 : Gel

A viscous gel preparation was produced from the following ingredients:

| | |
|---|---|
| AZT | 3% |
| Azone | 3% |
| N-methyl-2-pyrrolidone | 20% |
| Carbopol 934 | 1% |
| hydroxypropyl cellulose-M | 3% |
| 10% NaOH | appropriate volume |
| deionized water to make up | 100% |

Formulation 8 : Gel

A viscous gel preparation was produced from the following ingredients:

| | |
|---|---|
| AZT | 3% |
| Sefsol-318 | 5% |
| oleic acid | 10% |
| propylene glycol | 20% |
| N-methyl-2-pyrrolidone | 10% |
| gelatin | 3% |
| polyvinyl alcohol | 2% |
| sodium acrylate | 6% |
| deionized water to make up | 100% |

Formulation 9 : Tape

The ingredients given in Formulation 7 or 8 were mixed and coated on a tape film such that the tape contains 10 μmol AZT/cm$^2$ to give a tape preparation.

What is claimed is:

1. A percutaneous composition comprising AZT, as an effective ingredient together with an absorption promoting agent in an amount effective for assisting percutaneous absorption of AZT through the human skin, wherein said absorption promoting comprises 1-dodecylazacycloheptane-2-one used in combination with N-methyl-2-pyrrolidone, and wherein AZT is in a range from 0.5 to 10% by weight of the percutaneous composition and said absorption promoting agent is in a range from 0.1 to 40% by weight of the percutaneous composition.

2. A percutaneous composition as claimed in claim 1, wherein said composition is formulated as a gel.

3. A percutaneous composition as claimed in claim 1 or 2, wherein 1-dodecylazacycloheptane-2-one and N-methyl-2-pyrrolidone are contained in the absorption promoting agent at a ratio by weight of about 3:20.

4. A method of administering AZT in a percutaneous composition to an AIDS patient who is in need of treatment with AZT, comprising applying AZT to the skin of said patient together with an absorption promoting agent capable of assisting absorption of AZT through the skin into the blood stream of said patient, wherein said absorption promoting agent comprises 1-dodecylazacycloheptane-2-one used in combination with N-methyl-2-pyrrolidone and wherein AZT is in a range from 0.5 to 10% by weight of the percutaneous composition and said absorption promoting agent is in a range from 1 to 40% by weight of the percutaneous composition.

5. A method as claimed in claim 4, wherein 20–2,000 mg of AZT at a time is applied to the skin.

6. A method as claimed in claim 4 or 5, wherein 1-dodecylazacycloheptane-2-one and N-methyl-2-pyrrolidone are contained in the absorption promoting agent at a ratio by weight of about 3:20.

7. A method as claimed in claim 4, wherein AZT is applied to the skin area of less than about 300 cm$^2$ and an effective amount of AZT for the treatment of AIDS is absorbed by the skin.

8. A method as claimed in claim 4, wherein the effective AZT level in the plasma of the patient can be kept stable over a period of 10 hours or more.

* * * * *